United States Patent
Sherrod

[11] Patent Number: 5,979,444
[45] Date of Patent: Nov. 9, 1999

[54] PORTABLE CPR BREATHING APPARATUS

[76] Inventor: James B. Sherrod, 170 N. 600 West, Green River, Wyo. 82935

[21] Appl. No.: 08/877,228

[22] Filed: Jun. 17, 1997

[51] Int. Cl.⁶ ................................................. A61M 16/00
[52] U.S. Cl. .................. 128/205.25; 128/205.24; 128/204.25; 128/206.15; 128/207.12
[58] Field of Search ........................ 128/205.25, 201.13, 128/201.26, 206.29, 205.27, 206.21, 203.29, 205.24, 203.12, 204.26, 202.23, 207.12, 207.16, 206.15, 204.25, 204.29, 205.11, 203.17, 204.18

[56] References Cited

U.S. PATENT DOCUMENTS

| | | | |
|---|---|---|---|
| 3,485,243 | 12/1969 | Bird et al. | 128/204.25 |
| 3,556,409 | 1/1971 | Johannisson | 239/433 |
| 3,613,677 | 10/1971 | Blasko . | |
| 4,151,843 | 5/1979 | Brekke et al. | 128/205.25 |
| 4,197,842 | 4/1980 | Anderson | 128/203.12 |
| 4,244,361 | 1/1981 | Neubert | 128/200.14 |
| 4,470,413 | 9/1984 | Warncke | 128/201.18 |
| 4,706,683 | 11/1987 | Chilton et al. | 128/201.26 |
| 4,718,870 | 1/1988 | Watts | 440/47 |
| 4,719,911 | 1/1988 | Carrico | 128/206.29 |
| 4,741,332 | 5/1988 | Beaussant | 128/204.26 |
| 4,862,903 | 9/1989 | Campbell | 128/861 |
| 4,905,688 | 3/1990 | Vicenzi et al. | 128/204.21 |
| 5,088,485 | 2/1992 | Schock | 128/202.28 |
| 5,207,221 | 5/1993 | Stulbach | 128/206.29 |
| 5,211,170 | 5/1993 | Press | 128/204.18 |
| 5,370,112 | 12/1994 | Perkins | 128/204.21 |
| 5,381,783 | 1/1995 | Hintz | 128/206.29 |
| 5,386,822 | 2/1995 | Jones | 128/203.11 |
| 5,398,676 | 3/1995 | Press et al. | 128/204.23 |
| 5,503,146 | 4/1996 | Froehlich et al. | 128/205.25 |
| 5,526,805 | 6/1996 | Lutz et al. | 128/202.13 |
| 5,540,218 | 7/1996 | Jones et al. | 128/205.11 |
| 5,697,361 | 12/1997 | Smith | 128/204.18 |

OTHER PUBLICATIONS

*Effectiveness of Bystander Cardiopulmonary Resuscitation and Survival Following Out–of–Hospital Cardiac Arrest*, E. John Gallagher, M.D.; Gary Lombardi, M.D.; and Paul Gennis, M.D., JAMA Dec. 27, 1995, vol. 274, No. 24, pp. 1922–1925.

*Primary Examiner*—John G. Weiss
*Assistant Examiner*—V. Srivastava
*Attorney, Agent, or Firm*—Clayton, Howarth & Cannon, P. C.

[57] ABSTRACT

A breathing assisting device. The device includes a face mask and an oxygen dispenser which alternately injects oxygen (i) into the mask during an inhalation phase, and (ii) into a conveying piece which in turn conveys the oxygen through the mask during an exhalation phase in a manner which produces a subatmospheric pressure, or suction, within the mask during the exhalation phase, thereby assisting the user with both inhalation and exhalation.

33 Claims, 4 Drawing Sheets

PORTABLE CPR BREATHING APPARATUS

BACKGROUND OF THE INVENTION

1. The Field of the Invention

The present invention relates generally to portable resuscitation devices. More particularly, it concerns a portable device capable of both injecting air into, and withdrawing air from, a patient's mouth.

2. The Background Art

It is common practice to provide oxygen to an non-breathing person as part of a cardiopulmonary resuscitation process. In order to resuscitate a non-breathing person, it is known to try to force oxygen into the person's lungs as soon as possible. Prior art apparatus for accomplishing such a purpose involve large oxygen tanks and related machinery which are bulky and cumbersome and must often be transported by ambulance to the non-breathing patient.

Bystander cardiopulmonary resuscitation (CPR) is often the only option available for treating a non-breathing person. A Bystander performs CPR, including mouth-to-mouth breathing which usually only provides 10% to 20% oxygen content to the lungs, is often insufficient for the purposes of resuscitation and prevention of brain damage. The problem in compounded by the fact that a majority of CPR administrations are preformed improperly. One recent study was published to reveal that only 46% of the Bystander CPR cases included in the study were performed effectively; further, only 4.6% of those receiving effective CPR survived, while only 1.4% of those receiving ineffective CPR survived. Gallagher, et al., "Effectiveness of Bystander Cardiopulmonary Resuscitation and Survival Following Out-of-Hospital Cardiac Arrest," Journal of the American Medical Association, Vol. 274, No. 24, 1922–25 (Dec. 27, 1995).

Attempts have been made in the prior art to provide alternatives to Bystander CPR, in the design of portable resuscitation devices. U.S. Pat. No. 3,613,677 (granted Oct. 19, 1971 to Blasko) discloses a portable resuscitator carried in a box with a handle. This device is characterized by several disadvantages, including the need for a bellows device to mix oxygen from a storage bottle with ambient air. The device is designed such that only a limited amount of oxygen can be carried, and the oxygen is therefore supplemented by ambient air which reduces the effectiveness of the device.

There are several other portable resuscitation devices known in the prior art, such as that disclosed in U.S. Pat. No. 4,197,842 (granted Apr. 15, 1980 to Anderson). This patent reference discloses a portable resuscitation device which requires complex electronic control circuitry to provide selectivity between blower operation for I.P.P.B. breathing or alternatively emergency oxygen breathing, as well as other options. This device is expensive to manufacture and complex in operation.

It is noteworthy that none of the prior art known to applicant provides a resuscitation device capable of evacuating air from a patients mouth during the exhalation phase of the resuscitation. There is a long felt need, illustrated by the sobering statistics of low survival rates resulting from Bystander CPR as well as the disadvantageous resuscitation devices currently known, for a portable device which is inexpensive to make, simple in operation and which completes the resuscitation cycle by not only providing oxygen during inhalation but also evacuating air from the patient's mouth during the exhalation phase.

OBJECTS AND SUMMARY OF THE INVENTION

It is therefore an object of the present invention to provide a breathing assist device which is simple in design and manufacture.

It is another object of the present invention to provide such a breathing assist device capable of exposing a patient's mouth to subatmospheric pressure.

It is further object of the present invention, in accordance with one aspect thereof, to provide a breathing assist device which is portable and capable of being carried by hand.

It is an additional object of the invention, in accordance with one aspect thereof, to provide a breathing assist device capable of taking power selectively from either a take-along battery or alternatively from a cigarette lighter outlet in an automotive vehicle.

The above objects and others not specifically recited are realized in a specific illustrative embodiment of a breathing assisting device. The device includes a face mask and an oxygen dispenser which alternately injects oxygen (i) into the mask during an inhalation phase, and (ii) into a conveying piece which in turn conveys the oxygen through the mask during an exhalation phase in a manner which produces a subatmospheric pressure, or suction, within the mask during the exhalation phase, thereby assisting the user with both inhalation and exhalation.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF PRESENTLY PREFERRED EMBODIMENTS

Figure 1:
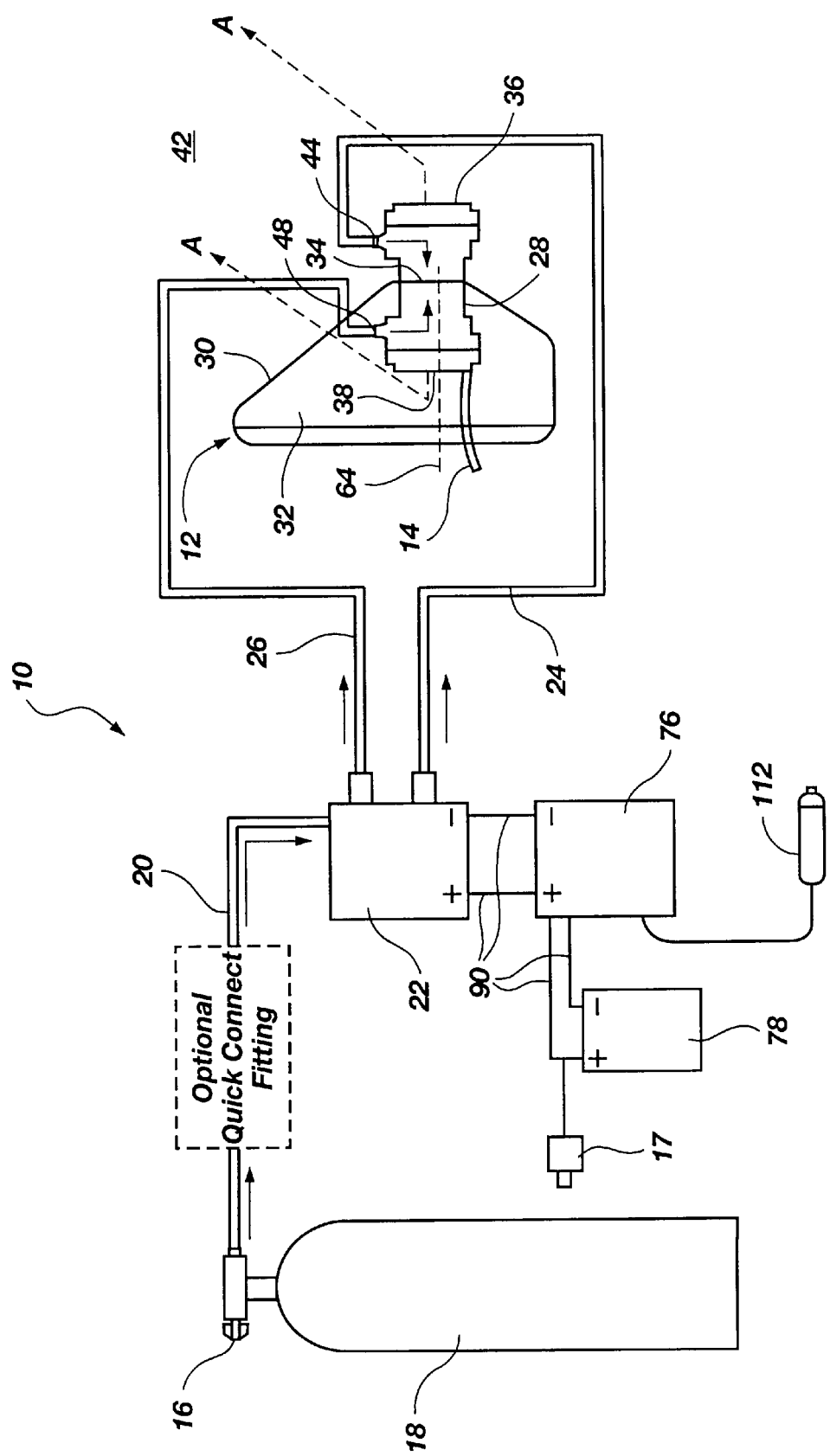
FIG. 1 is a schematic view of a breathing assist device made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated device, and any additional applications of the principles of the invention as illustrated herein, which would normally occur to one skilled in the relevant art and possessed of this disclosure, are to be considered within the scope of the invention claimed.

Applicant has conceived of a breathing assist device capable of injecting oxygen into the lungs as well as withdrawing air from the mouth under subatmospheric pressure. A preferred design concept includes an airflow passage formed either as a part of an oxygen mask, or as a removable piece, which channels airflow under pressure through a portion of the mask in a manner which produces a subatmospheric pressure, or suction, within the mask responsive to the airflow movement during an exhalation phase.

Figure 2:
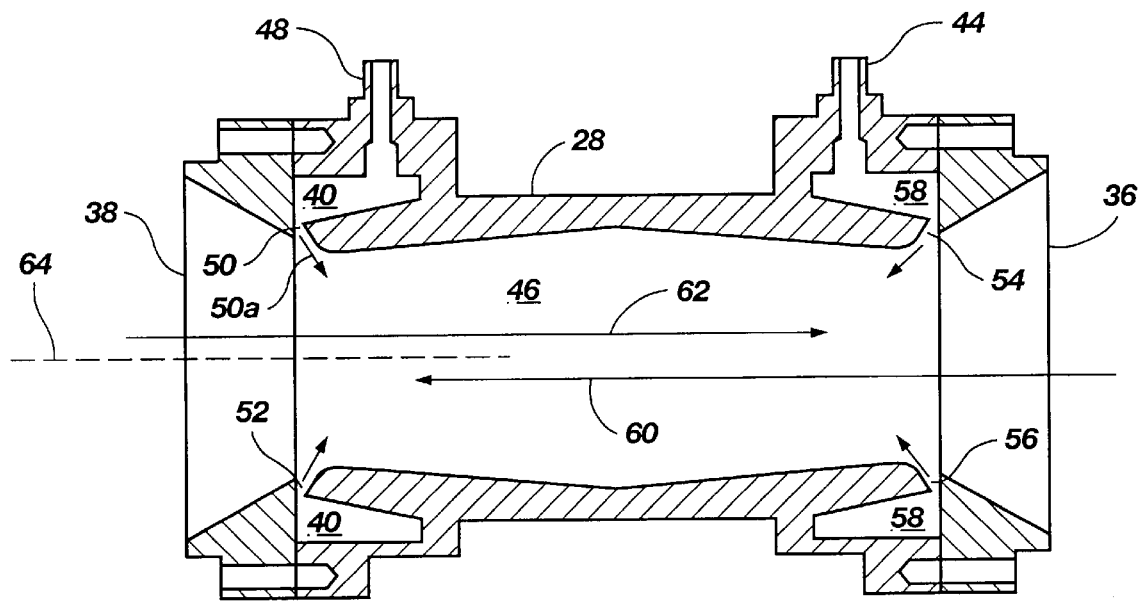
FIG. 2 is a side, cross-sectional view of an air amplifier portion of the breathing assist device of FIG. 1, taken along section A—A.

Referring now to FIGS. 1-2, there is shown a breathing assist device, designated generally at 10. In operation, a user treating a patient (not shown) in need of breathing assist procedures places a face mask means 12 over a mouth (not shown) of the patient, inserting a tongue depressor 14 into the mouth and over the patient's tongue in the process. The user then actuates an actuation switch 16 (as well as a switch 17 if present) which releases oxygen from oxygen bottle 18 into flow tubing 20, and a regulator valve 22 operates to channel the oxygen into the inhalation tube 24 and the exhalation tube 26 in alternating tandem such that oxygen flows within only one of the tubes 24 and 26 at any given time. In this manner the alternating oxygen flow is received by conveying piece 28 which produces therewith alternating inhalation and exhalation phases, during which oxygen is conveyed to the patient in the inhalation phase and air is withdrawn from the patient's mouth in the exhalation phase.

The face mask means 12 comprises a means for being placed over a mouth of the patient, said face mask means 12 including (i) a concave mask body 30 defining an interior mask volume 32 and having an outlet port 34, and (ii) the conveying piece 28 disposed at least partially within the interior mask volume 32 and having a first open end 36, a second open end 38, and an annular passage 40 (not shown in FIG. 1) disposed in communication with both the interior mask volume 32 and with an atmosphere 42 external to the mask body 30.

It will be appreciated that the structure and apparatus disclosed herein is merely one example of a face mask means 12 for being placed over a mouth of the patient, and it should be appreciated that any structure, apparatus or system for being placed over a patient's mouth which performs functions the same as, or equivalent to, those disclosed herein are intended to fall within the scope of a face mask means for being placed over a mouth of the patient, including those structures, apparatus or systems for being placed over a patient's mouth which are presently known, or which may become available in the future. Anything which functions the same as, or equivalently to, a face mask means for being placed over a mouth of the patient falls within the scope of this element.

The breathing assist device 10 further includes a first air inlet 44 disposed in communication with the interior mask volume 32 because the conveying piece 28 includes a throughpassage 46 (not shown in FIG. 1) which accomplishes such communication. The first air inlet 44 delivers air from the inhalation tube 24 to the patient's mouth when the face mask means 12 is placed over the patient's mouth.

A second air inlet 48 is disposed in communication with the annular passage 40, which communicates with the atmosphere 42 external to the mask body 30 through a passage 50 that is angled directionally toward the outlet port 34 of the mask body 30 in a manner sufficient to cause air injected into the second air inlet 48 to pass sequentially through the annular passage 40 and out through said outlet port 34 to said atmosphere such that a subatmospheric pressure is thereby produced at the first open end of the conveying piece 28, as a byproduct of the air moving from said second air inlet 48 through said outlet opening 34. The conveying piece 28 may itself extend through the outlet port 34, and it will be understood that anything which advances through the throughpassage 46 also advances through the outlet port 34 thereby.

Referring now more particularly to FIG. 2, the conveying piece 28 is designed such that air injected through first air inlet 44 advances sequentially through annular passage 58, first connecting passages 54 and 56, and thereafter through the throughpassage 46 in a direction indicated by arrow 60 and out through the second open end 38 into the interior mask volume 32 (shown in FIG. 1) for breathing access by a patient, an activity which produces a subatmospheric pressure at first open end 36. Similarly, air injected through the second air inlet 48 advances sequentially through annular passage 40, second connecting passages 50 and 52, and thereafter through the throughpassage 46 in a direction indicated by arrow 62 and out through the first open end 36 into the atmosphere 42, an activity which produces a subatmosphere pressure at second open end 38.

Those having ordinary skill in the relevant field of fluid mechanics will appreciate that the production of subatmospheric pressure occurs as a byproduct of air movement through the conveying piece 28. As air is forced through the piece 28 in the direction of arrow 62, subatmospheric pressure occurs at the open end 38. Conversely, as air is forced through the piece 28 in the direction of arrow 60, subatmospheric pressure occurs at the open end 36.

The mask body 30 defines a central axis 64 extending through the outlet port 34, and the connecting passage 50 defines an acute angle with respect to said central axis 64. The phrase "angled directionally toward" as used herein shall include the concept that a directional orientation may have different components of direction. For example, the connecting passage 50 is angled as shown by arrow 50*a* which, with respect to the axis 64 has one component of direction extending parallel to said axis 64 and thus toward the first open end 36, and a second component of direction extending orthogonally to said axis 64, as can be appreciated by those of ordinary skill in the relevant physics. Accordingly, the first connecting passage 50 is angled directionally toward the first open end 36.

The conveying piece 28 is preferably removably attached within the mask body 30. For example, the first air inlet 44 may be detachable so as to enable passage of the piece 28 through the outlet port 34 and from the mask body 30.

Figure 3:
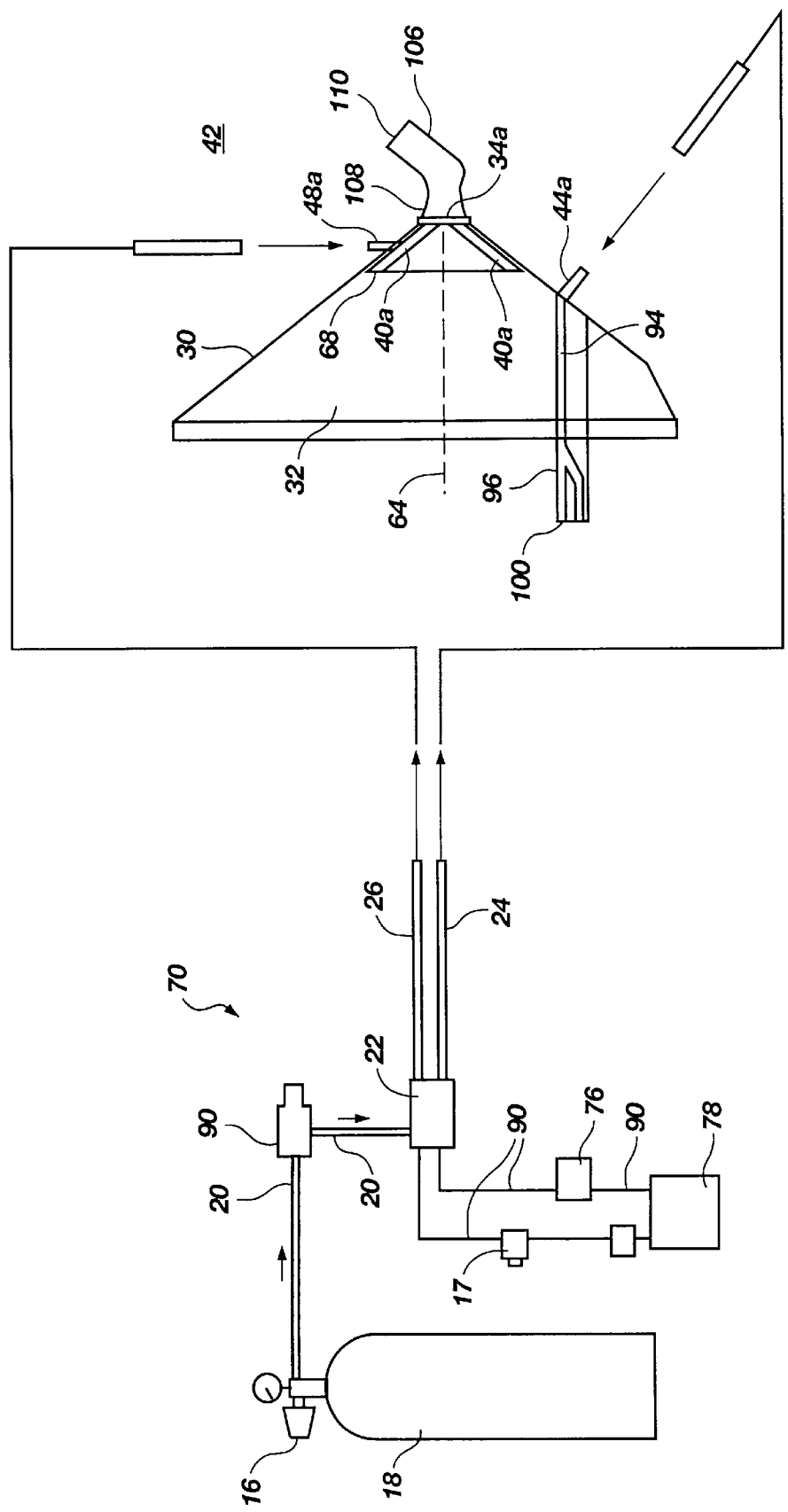
FIG. 3 is a schematic view of an alternative embodiment of the breathing assist device of FIG. 1.

Referring now to FIG. 3, the conveying piece may alternatively comprise a frusto-conical piece 68. The frusto-conical piece 68 includes an outer frusto-conical member 72 and an inner frusto-conical member 74 disposed within said outer frusto-conical member 72 in substantial co-axial orientation therewith.

Referring now collectively to FIGS. 1 and 3, FIG. 3 illustrates an alternative embodiment of the breathing assist device 10 of FIG. 1, in the form of device 70. However, the device 10 of FIG. 1 and the device 70 of FIG. 3 differ principally with respect to the respectively conveying pieces 28 (FIG. 1) and 68 (FIG. 3). Many of the other operative components are the same.

An air source means includes the oxygen bottle 18, flow tubing 20, regulator valve 22, inhalation tubing 24, exhalation tubing 26, a timer 76, and power source 78. The air source means comprises a means for performing the following steps in alternating tandem:

(i) injecting air into the first inlet passage 44 (44*a* in FIG. 3) to thereby convey airflow into the interior mask volume 32 and into the patient's mouth, and (ii) injecting air into the second air inlet passage 48 (48*a* in FIG. 3) to thereby convey airflow through the annular passage 40 (40*a* in FIG. 3) and the outlet port 34 (34*a* in FIG. 3) in a manner sufficient to produce a subatmospheric pressure within the interior mask volume 32.

Figure 4A:
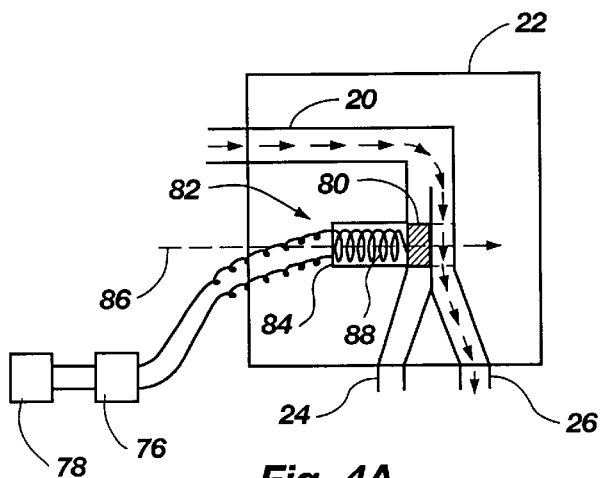
FIG. 4A is a schematic view of a regulator valve of the breathing assist devices of FIG. 1 and FIG. 3, in a first position.
Figure 4B:
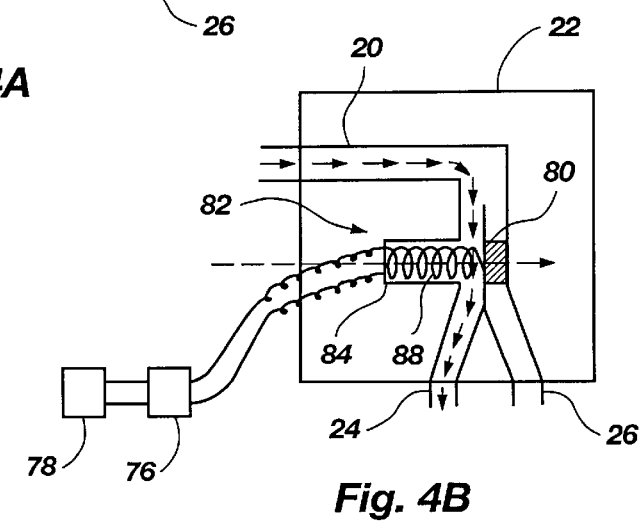
FIG. 4B is a schematic view of the regulator valve of FIG. 4A in a second position.

The inhalation tubing 24 may be described as a first airflow passage disposed in communication with the first inlet passage 44 (44*a* in FIG. 3), and the exhalation tubing 26 may be described as a second airflow passage disposed in communication with the second inlet passage 48 (48*a* in FIG. 3). The regulator valve 22 and timer 76 may be described as a regulator means for blocking a releasing airflow within the first and second airflow passage in alternating tandem. Referring more particularly to FIGS. 4A–4B, the regulator valve 22 includes a blocking member 80 configured and dimensioned for being removably placed within either the first airflow passage 24 or the second airflow passage 26 for blocking airflow within said passages, and a moving means 82 for alternately moving the blocking member 80 (i) from the first airflow passage 24 into the second airflow passage 26, and (ii) from the second airflow passage 26 into the first airflow passage 24.

The moving means 82 preferably, but not necessarily, comprises a solenoid member 84, a timer-controlled power source (preferably in the form of power source 78 and timer 76), for alternately powering and unpowering the solenoid member 84 to thereby alternately produce and suspend a magnetic force extending within the solenoid member 84 along a magnetic force path 86, and a retaining means 88 coupled to the blocking member 80 for imposing a retention force upon said blocking member 80 opposite in direction to the magnetic force. The retaining means 88 is preferably a spring coupled to the blocking member 80.

The blocking member 80 resides within the magnetic force path 86 and within the first airflow passage 24 in an initial position as shown in FIG. 4A such that (i) when the magnetic force imposes a force upon said blocking member 80 in excess of the retention force provided by retaining member 88 said blocking member 80 is thereby forced responsively into the second airflow passage 26 as shown in FIG. 4B, and (ii) when the magnetic force is suspended the retention force compels said blocking member 80 back into the initial position of FIG. 4A. In this manner the blocking member 80 simply moves back and forth to alternately block airflow in the passages 24 and 26.

Referring to FIGS. 4A–4B and FIGS. 1 and 3, when airflow is blocked in the second or exhalation passage 26, airflow is conveyed through the first or inhalation passage 24 and into the interior mask volume 32 for the patient to inhale. When the blocking member 80 is then forced into the first or inhalation passage 24, airflow is blocked therein but permitted to pass through the second or exhalation passage 26, and through the second inlet passage 48 (FIG. 1) or 48*a* (FIG. 3), then through the annular passage 40 (FIG. 1) or 40*a* (FIG. 3) and out through the outlet port 34 (FIG. 1) or 34*a* (FIG. 3), thereby producing a subatmospheric pressure within the interior mask volume 32 for withdrawing air from the patient's mouth.

It will be appreciated that the structure and apparatus disclosed herein is merely one example of a regulator means 22 for blocking and releasing airflow within two or more air passages, and it should be appreciated that any structure, apparatus or system for blocking and releasing which performs functions the same as, or equivalent to, those disclosed herein are intended to fall within the scope of a means for blocking and releasing, including those structures, apparatus or systems for blocking and releasing which are presently known, or which may become available in the future. Anything which functions the same as, or equivalently to, a means for blocking and releasing falls within the scope of this element.

It will further be appreciated that the structure and apparatus disclosed herein is merely one example of a moving means 82 for moving another member (such as the blocking member 80), and it should be appreciated that any structure, apparatus or system for moving another member which performs functions the same as, or equivalent to, those disclosed herein are intended to fall within the scope of a means for moving, including those structures, apparatus or systems for moving which are presently known, or which may become available in the future. Anything which functions the same as, or equivalently to, a means for moving falls within the scope of this element.

The oxygen bottle 18 operates as an air dispensing means for dispensing air into the first and second airflow passages 24 and 26, respectively. A pressure regulator 90 may be used as shown in FIG. 1 as a pressure control means for selectively altering air pressure of air dispensed by the oxygen bottle 18.

One important aspect in accordance with the principles of the present invention is convenient portability. More specifically, it is preferred that the group consisting of the power source 78, the timer 76, the pressure regulator 90 and the regulator valve 22 collectively constitute less than 2.0 cubic feet in volume. Further, the face mask means 12 and the oxygen bottle 18 and the members of said group (power source 78, timer 76, pressure regulator 90 and regulator valve 22) are operatively interconnected with flexible members, such as flexible flow tubing 20, flexible passages 24 and 26 and flexible electrical wiring 92 to thereby render the entire breathing assist device portable and carryable by a user. The aforementioned group (power source 78, timer 76, pressure regulator 90 and regulator valve 22) most preferably constitutes less than 1.0 cubic feet in volume, collectively.

Figure 3B:
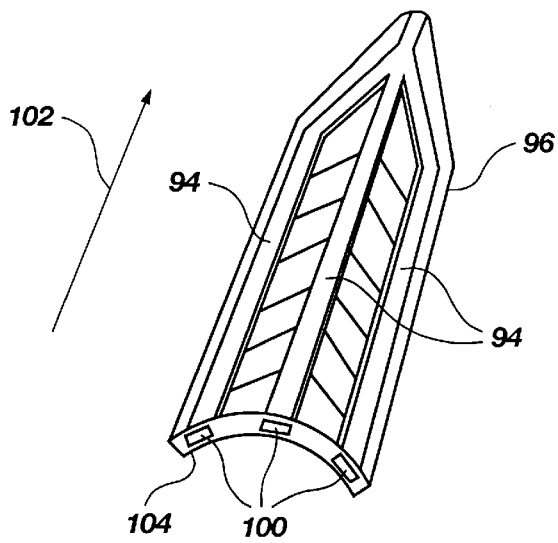
FIG. 3B is a perspective view of a tongue depressor portion of the breathing assist device of FIG. 3.
Figure 3A:
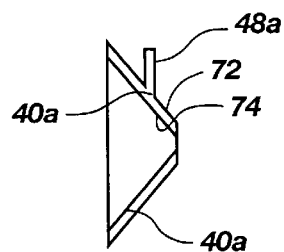
FIG. 3A is side view of a conveying piece of the breathing assist device of FIG. 3.

Referring now to FIGS. 3, 3A and 3B, which disclose alternative embodiments of the invention, it will be appreciated that the frusto-conical piece 68 operates to produce a subatmospheric pressure within the interior mask volume 32 in the same manner as the conveying piece 28 of FIG. 1. The frusto-conical piece 68 comprises an outer frusto-conical member 72 and an inner frusto-conical member 74 disposed within said outer frusto-conical member 72 in substantial co-axial orientation therewith. In this embodiment, the conveying piece 68 is not used in conjunction with supplying air to the patient during the inhalation phase; instead, the inhalation tube 24 is connecting to the air inlet 44*a* which channels air through internal air channels 94 formed within a tongue depressor 96.

The conveying piece 68 is used principally in conjunction with the exhalation feature of producing subatmospheric pressure within the interior mask volume 32. The inner and outer frusto-conical members 74 and 72 define an annular passage 40a therebetween which is itself frusto-conical in shape, and is therefore angled in a tapering fashion radially inwardly in a proximal-to-distal direction toward the outlet port 34a. When air is injected into first air inlet 48a, it is naturally channeled through the annular channel 40a through the outlet port 34a, thereby providing an airflow which produces suction, or subatmospheric pressure, within the interior mask volume 32.

Accordingly, the tongue depressor 96 is disposed at least partially within the interior mask volume 32 and has at least one internal air channel 94 formed therein, said internal air channel 94 being disposed in communication with the first air inlet 48a and terminating in a discharge opening 100 for conveying air from said first air inlet 48a to said discharge opening 100. Referring to FIG. 3B, the tongue depressor 96 preferably includes a plurality of internal air channels 94 terminating in a plurality of air discharge openings 100 in the proximal end, respectively, is said tongue depressor 96. The tongue depressor 96 has a longitudinal length as shown, and is arcuately curved about an axis extending in the longitudinal direction 102 to thereby define a trough-shaped, concavo-convex member having a concave under surface 104 defining a longitudinal trough for receiving a tongue of the patient thereinto.

The mask body 30 defines a central axis 64 extending through the outlet port 34a, said device further comprising a tubular elbow 106 having a first open end 108 disposed in communication with the outlet port 34a of the mask body 30, and an opposing second open end 110 exposed to atmosphere 42, said elbow 106 being rotatably coupled to the mask body 30 and terminating in a free end which defines the second open end 110 and which is angled directionally away from the central axis 64 of the mask body 30 and the outlet port 34a.

It is to be understood that the scope of the present invention includes the broad concept of a single breathing assist device capable of both injecting air into a patient's mouth and introducing subatmospheric pressure to said patient's mouth during an exhalation phase. It will be appreciated that the structure and apparatus disclosed herein is merely one example of means for injecting air into a patient's mouth and withdrawing air from said patient's mouth under subatmospheric pressure, and it should be appreciated that any structure, apparatus or system for injecting or suctioning which performs functions the same as, or equivalent to, those disclosed herein are intended to fall within the scope of injecting means for injection and suction means for suctioning (or introducing subatmospheric pressure), including those structures, apparatus or systems which are presently known, or which may become available in the future. Anything which functions the same as, or equivalently to, a means for injecting or a means for suctioning falls within the scope of these elements.

In accordance with the features and combinations described above, a preferred method of assisting a patient's breathing includes the steps of:

(a) injecting air into a mouth of the patient through a first tube which is coupled to a mask disposed on a face of the patient; and (b) withdrawing air from the mouth of the patient through a second tube which is coupled to the mask and not disposed in direct communication with the first tube.

Figure 2A:
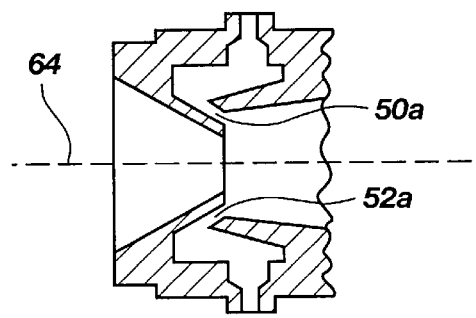
FIG. 2A is a side, break-away cross-sectional view of an alternative embodiment of the air amplifier of FIG. 2.

It will be appreciated that the connecting passages 50, 52, 54 and 56 formed in the conveying piece 28 may comprise any suitable passage or passages which provide an airflow path angled in direction with respect to the central axis 64 of the mask body 30 and toward an opposing end of the conveying piece 28. For example, the passages 50, 52, 54 and 56 are shown as openings which have a rear lateral side orthogonal to the central axis 64, and an opposing outwardly-flared angled side. Alternatively and in reference to FIG. 2A, these passages may comprise cylindrical channels such as those shown at 50a and 52a which are angled directionally with respect to the central axis 64. Regardless of shape or form, the connecting passages preferably comprise four equidistantly spaced passages at each end of the conveying piece 28.

FIG. 1 illustrates yet another aspect of portability of the breathing assist device 10. The device 10 is capable of taking power selectively from either the power source 78 (preferably a take-along battery as shown) or alternatively from a cigarette lighter outlet in an automotive vehicle (not shown) via an outlet interface 112. The outlet interface may of course be utilized with the alternative embodiment 70 of the invention, or with any other alternative embodiment.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A breathing assist device for providing air to a patient comprising:

face mask means for being placed over a mouth of a patient, said face mask means including (i) a concave mask body defining an interior mask volume and having an outlet port, and (ii) a conveying piece disposed at least partially within the interior mask volume and having a first open end, a second open end, and an annular passage disposed in communication with the interior mask volume and with an atmosphere external to the mask body;

a first air inlet disposed in communication with the interior mask volume for delivering air to the patient's mouth when the face mask means is placed over said patient's mouth, and a second air inlet disposed in communication with the annular passage;

wherein at least a portion of the annular passage communicates with said atmosphere external to the mask body through a passage angled directionally toward the outlet port of the mask body in a manner sufficient to cause air injected into the second air inlet to pass sequentially through the annular passage and out through said outlet port to said atmosphere such that a subatmospheric pressure is thereby produced at the first open end of the conveying piece as a byproduct of the air moving from said second air inlet through said outlet port.

2. The breathing assist device of claim 1, wherein the mask body defines a central axis extending through the outlet port, and wherein at least a portion of the annular passage defines an acute angle with respect to said central axis.

3. The breathing assist device of claim 1, wherein the conveying piece further includes a central through passage surrounded by said annular passage, said through passage extending between the first open end and the second open end of said conveying piece.

4. The breathing assist device of claim 3, wherein the conveying piece is removably attached within the mask body.

5. The breathing assist device of claim 4, wherein the conveying piece comprises an outer frusto-conical member and an inner frusto-conical member disposed within said outer frusto-conical member in substantial co-axial orientation therewith.

6. The breathing assist device of claim 1, further comprising:
   air source means for performing the following steps in alternating tandem:
   (i) injecting air into the first inlet passage to thereby convey airflow into the interior mask volume and into the patient's mouth, and
   (ii) injecting air into the second air inlet passage to thereby convey airflow through the annular passage and the outlet port in a manner sufficient to produce a subatmospheric pressure within the interior mask volume.

7. The breathing assist device of claim 6, wherein the air source means further comprises:
   a first airflow passage disposed in communication with the first inlet passage;
   a second airflow passage disposed in communication with the second inlet passage; and
   regulator means for blocking and releasing airflow within the first and second airflow passages in alternating tandem.

8. The breathing assist device of claim 7, wherein the regulator means comprises:
   a blocking member configured and dimensioned for being removably placed within either the first airflow passage or the second airflow passage for blocking airflow within said passages; and
   moving means for alternately moving the blocking member (i) from the first airflow passage into the second airflow passage, and (ii) from the second airflow passage into the first airflow passage.

9. The breathing assist device of claim 8, wherein the moving means comprises:
   a solenoid member;
   a timer-controlled power source for alternately powering and unpowering the solenoid member to thereby alternately produce and suspend a magnetic force extending within the solenoid member along a magnetic force path;
   a retaining means coupled to the blocking member for imposing a retention force upon said blocking member opposite in direction to the magnetic force;
   wherein the blocking member resides within the magnetic force path and within one of the airflow passages in an initial position such that (i) when the magnetic force imposes a force upon said blocking member in excess of the retention force said blocking member is thereby forced responsively into the other of the airflow passages, and (ii) when the magnetic force is suspended the retention force compels said blocking member back into the initial position.

10. The breathing assist device of claim 9, wherein the retaining means comprises a spring coupled to the blocking member.

11. The breathing assist device of claim 7, wherein the air source means further comprises:
    air dispensing means disposed in communication with the first and second airflow passages for dispensing air into said airflow passages;
    pressure control means for selectively altering air pressure of the air dispensed by the air dispensing means;
    timing means for controlling a rate at which the regulator means alternately blocks and releases airflow within the first and second airflow passages; and
    power source means for powering the regulator means.

12. The breathing assist device of claim 11, wherein a group consisting of the power source means, the timing means, the pressure control means and the regulator means constitutes less than 2.0 cubic feet in volume, and wherein the face mask means and the air source means and the members of said group are operatively interconnected with flexible members to thereby render the entire breathing assist device portable and carryable by a user.

13. The breathing assist device of claim 12, wherein the group consisting of the power source means, the timing means, the pressure control means and the regulator means constitutes less than 1.0 cubic feet in volume.

14. The breathing assist device of claim 1, further comprising:
    a tongue depressor disposed at least partially within the interior mask volume and having at least one internal air channel formed therein, said internal air channel being disposed in communication with the first air inlet and terminating in a discharge opening for conveying air from said first air inlet to said discharge opening.

15. The breathing assist device of claim 14, wherein the tongue depressor has a longitudinal length and is arcuately curved about an axis extending in the longitudinal direction to thereby define a trough-shaped, concavo-convex member having a concave under surface defining a longitudinal trough for receiving a tongue of a patient thereinto.

16. The breathing assist device of claim 14, wherein the tongue depressor comprises a distal end intercoupled to the first air inlet and an opposing proximal end for inserting into the patient's mouth, said tongue depressor including an air inlet port formed in the distal end and a plurality of internal air channels terminating in a plurality of air discharge openings in the proximal end, respectively.

17. The breathing assist device of claim 1, wherein the mask body defines a central axis extending through the outlet port, said device further comprising a tubular elbow having a first open end disposed in communication with the outlet port of the mask body, and an opposing second open end exposed to atmosphere, said elbow being rotatably coupled to the mask body and terminating in a free end which defines the second open end and which is angled directionally away from the central axis of the mask body and the outlet port.

18. The breathing assist device of claim 1, wherein the conveying piece comprises a bi-directional conveying piece defining the annular passage, said conveying piece further comprising:
    a channel body comprised of sidewalls forming a central through passage extending between the first open end and the opposing second open end, and wherein the annular passage comprises a first annular passage formed in said sidewalls and wherein the first air inlet is formed in said channel body;
    a second annular passage formed in the sidewalls of the channel body, said first and second annular passages encircling the central through passage;
    at least a first connecting passage formed in the sidewalls in communication with the first annular passage and the central through passage, said first connecting passage being angled directionally toward the second opening of the channel body; and
    a second air inlet formed in the channel body, and at least a second connecting passage formed in the sidewalls in communication with the second annular passage and the central through passage, said second connecting passage being angled directionally toward the first opening of the channel body.

19. The breathing assist device of claim 18, wherein the annular passages, connecting passages and central through passage are configured and arranged in a manner sufficient to (i) cause air injected into the first air inlet to pass sequentially through the first annular passage, first connecting passage, and the second opening of the channel body into the patient's mouth, and (ii) cause air injected into the second air inlet to pass sequentially through the second annular passage, second connecting passage and out of the first opening of the channel body such that a subatmospheric pressure is thereby produced at the second opening as a byproduct of the air moving from said second inlet through said second opening to thereby withdraw air from the patient's mouth.

20. The breathing assist device of claim 18, wherein the channel body extends through the outlet port of the mask body such that the second air inlet reside within the interior mask volume and the first air inlet reside outside said interior mask volume.

21. The breathing assist device of claim 18, wherein the channel body comprises a first end on which the first inlet is formed and an opposing second end on which the second inlet is formed, the breathing assisting device further comprising a tongue depressor attached to the second end of the channel body and extending outwardly therefrom for protruding into the patient's mouth and residing atop a tongue of the patient when the face mask means is covering said patient's mouth.

22. The breathing assist device of claim 1, wherein the annular passage includes a first open annular end disposed within the interior mask volume and a second open annular end disposed in communication with the outlet port of the mask body.

23. The breathing assist device of claim 7, wherein the air source means further comprises:
    air dispensing means disposed in communication with the first and second airflow passages for dispensing air into said airflow passages; and
    power source means for powering the regulator means, said power source means comprising either a take-along battery or an outlet interface means for receiving power from a heat-lighter outlet in an automotive vehicle.

24. A breathing assist device for providing air to a patient comprising:
    injecting means for injecting air into a mouth of a patient, said injecting means including a first airflow passage;
    suction means coupled to the injecting means for introducing subatmospheric pressure to the patient's mouth and thereby withdrawing air from said patient's mouth, said suction means including a second airflow passage; and
    regulator means for blocking and releasing airflow within the first and second airflow passages in alternating tandem;
    wherein the regulator means comprises:
        a blocking member configured and dimensioned for being removably placed within either the first airflow passage or the second airflow passage for blocking airflow within said passages; and
        moving means for alternately moving the blocking member (i) from the first airflow passage into the second airflow passage, and (ii) from the second airflow passage into the first airflow passage.

25. The breathing assist device of claim 24, wherein the moving means comprises:
    a solenoid member;
    a timer-controlled power source for alternately powering and unpowering the solenoid member to thereby alternately produce and suspend a magnetic force extending within the solenoid member along a magnetic force path;
    a retaining means coupled to the blocking member for imposing a retention force upon said blocking member opposite in direction to the magnetic force;
    wherein the blocking member resides within the magnetic force path and within one of the airflow passages in an initial position such that (i) when the magnetic force imposes a force upon said blocking member in excess of the retention force said blocking member is thereby forced responsively into the other of the airflow passages, and (ii) when the magnetic force is suspended the retention force compels said blocking member back into the initial position.

26. The breathing assist device of claim 25, wherein the retaining means comprises a spring coupled to the blocking member.

27. A breathing assist device for providing air to a patient comprising:
    injection means for injecting air into a mouth of a patient; and
    suction means for introducing subatmospheric pressure to the patient's mouth and thereby withdrawing air from said patient's mouth;
    wherein the injection means and the suction means collectively comprise:
        a concave mask body defining an interior mask volume and having an outlet port;
        a conveying piece disposed at least partially within the interior mask volume and having a first open end, a second open end, and an annular passage disposed in communication with the interior mask volume and with an atmosphere external to the mask body;
        a first air inlet disposed in communication with the interior mask volume for delivering air to the patient's mouth when the mask body is placed over said patient's mouth, and a second air inlet disposed in communication with the annular passage.

28. The breathing assist device of claim 27, wherein the conveying piece comprises a bi-directional conveying piece defining the annular passage, said conveying piece further comprising:
    a channel body comprised of sidewalls forming a central through passage extending between the first open end and the opposing second open end, and wherein the annular passage comprises a first annular passage formed in said sidewalls and wherein the first air inlet is formed in said channel body;
    a second annular passage formed in the sidewalls of the channel body, said first and second annular passages encircling the central through passage;
    at least a first connecting passage formed in the sidewalls in communication with the first annular passage and the central through passage, said first connecting passage being angled directionally toward the second opening of the channel body; and
    a second air inlet formed in the channel body, and at least a second connecting passage formed in the sidewalls in communication with the second annular passage and the central through passage, said second connecting passage being angled directionally toward the first opening of the channel body.

29. The breathing assist device of claim 27, wherein the conveying piece is removably attached within the mask body, and further comprises an outer frusto-conical member and an inner frusto-conical member disposed within said outer frusto-conical member in substantial co-axial orientation therewith.

30. A bi-directional air amplifier comprising:
   a channel body comprised of sidewalls forming a central through passage having a first end and an opposing second end;
   a first annular passage and a second annular passage formed in the sidewalls of the channel body, said annular passages encircling the central through passage;
   a first air inlet formed in the channel body, and at least a first connecting passage formed in the sidewalls in communication with the first annular passage and the central through passage, said first connecting passage being angled directionally toward the second end of the channel body; and
   a second air inlet formed in the channel body, and at least a second connecting passage formed in the sidewalls in communication with the second annular passage and the central through passage, said second connecting passage being angled directionally toward the first end of the channel body.

31. The bi-directional air amplifier of claim 30, wherein the annular passages, connecting passages and central through passage are configured and arranged in a manner sufficient to (i) cause air injected into the first air inlet to pass sequentially through the first annular passage, first connecting passage and out of the second end of the channel body such that a subatmospheric pressure is thereby produced at the first end as a byproduct of said air moving from said first inlet through said second end, and (ii) cause air injected into the second air inlet to pass sequentially through the second annular passage, second connecting passage and out of the first end of the channel body such that a subatmospheric pressure is thereby produced at the second end as a byproduct of said air moving from said second inlet through said second end.

32. The breathing assist device of claim 30, wherein the central through passage includes a largest diameter at a mid-portion thereof, said through passage flaring continuously outwardly (i) in a first direction from the first end to said largest diameter, and (ii) in an opposing second direction from the second end to said largest diameter.

33. A breathing assist device for providing air to a patient comprising:
   face mask means for being placed over a mouth of a patient, said face mask means including (i) a concave mask body defining an interior mask volume and having an outlet port, and (ii) a conveying piece disposed at least partially within the interior mask volume and having a first open end, a second open end, and an annular passage disposed in communication with the interior mask volume and with an atmosphere external to the mask body;
   a first air inlet disposed in communication with the interior mask volume for delivering air to the patient's mouth when the face mask means is placed over said patient's mouth, and a second air inlet disposed in communication with the annular passage;
   wherein at least a portion of the annular passage communicates with said atmosphere external to the mask body through a passage angled directionally toward the outlet port of the mask body in a manner sufficient to cause air injected into the second air inlet to pass sequentially through the annular passage and out through said outlet port to said atmosphere such that a subatmospheric pressure is thereby produced at the first open end of the conveying piece as a byproduct of the air moving from said second air inlet through said outlet opening;
   wherein the conveying piece further includes a central through passage surrounded by said annular passage, said through passage extending between the first open end and the second open end of said conveying piece;
   wherein the conveying piece is removably attached within the mask body;
   air source means for performing the following steps in alternating tandem:
      (i) injecting air into the first inlet passage to thereby convey airflow into the interior mask volume and into the patient's mouth, and
      (ii) injecting air into the second air inlet passage to thereby convey airflow through the annular passage and the outlet port in a manner sufficient to produce a subatmospheric pressure within the interior mask volume;
   wherein the air source means further comprises:
      a first airflow passage disposed in communication with the first inlet passage;
      a second airflow passage disposed in communication with the second inlet passage; and
      regulator means for blocking and releasing airflow within the first and second airflow passages in alternating tandem, the regulator means further comprising:
         a blocking member configured and dimensioned for being removably placed within either the first airflow passage or the second airflow passage for blocking airflow within said passages; and
         moving means for alternately moving the blocking member (i) from the first airflow passage into the second airflow passage, and (ii) from the second airflow passage into the first airflow passage, the moving means further comprising:
            a timer-controlled power source for alternately producing and suspending a first force along a first force path;
            a retaining means coupled to the blocking member for imposing a retention force upon said blocking member opposite in direction to the first force;
   wherein the blocking member resides within the first force path and within one of the airflow passages in an initial position such that (i) when the first force imposes a force upon said blocking member in excess of the retention force said blocking member is thereby forced responsively into the other of the airflow passages, and (ii) when the first force is suspended the retention force compels said blocking member back into the initial position;
   wherein the air source means further comprises:
      air dispensing means disposed in communication with the first and second airflow passages for dispensing air into said airflow passages;
      pressure control means for selectively altering air pressure of the air dispensed by the air dispensing means; and timing means for controlling a rate at which the regulator means alternately blocks and releases airflow within the first and second airflow passages;

wherein a group consisting of the times controlled power source, the timing means, the pressure control means and the regulator means collectively constitute less than 2.0 cubic feet in volume, and wherein the face mask means and the air source means and the members of said group are operatively interconnected with flexible members to thereby render the entire breathing assist device portable and carryable by a user;

wherein the mask body defines a central axis extending through the outlet port, said device further comprising a tubular elbow having a first open end disposed in communication with the outlet port of the mask body, and an opposing second open end exposed to atmosphere, said elbow being rotatably coupled to the mask body and terminating in a free end which defines the second open end and which is angled directionally away from the central axis of the mask body and the outlet port.

* * * * *